US009597402B2

(12) United States Patent
Luk et al.

(10) Patent No.: US 9,597,402 B2
(45) Date of Patent: *Mar. 21, 2017

(54) SUSTAINED RELEASE SMALL MOLECULE DRUG FORMULATION

(71) Applicant: DURECT CORPORATION, Cupertino, CA (US)

(72) Inventors: Andrew S. Luk, Castro Valley, CA (US); Gunjan H. Junnarkar, Palo Alto, CA (US); Guohua Chen, Sunnyvale, CA (US)

(73) Assignee: DURECT CORPORATION, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/701,173

(22) Filed: Apr. 30, 2015

(65) Prior Publication Data

US 2015/0231258 A1 Aug. 20, 2015

Related U.S. Application Data

(63) Continuation of application No. 13/790,930, filed on Mar. 8, 2013, now Pat. No. 9,044,450, which is a continuation of application No. 11/535,398, filed on Sep. 26, 2006, now Pat. No. 8,852,638.

(60) Provisional application No. 60/722,845, filed on Sep. 30, 2005.

(51) Int. Cl.
A61K 9/14 (2006.01)
A61K 47/34 (2006.01)
A61K 31/341 (2006.01)
A61K 31/519 (2006.01)
A61K 9/00 (2006.01)
A61K 51/12 (2006.01)
A61K 9/06 (2006.01)

(52) U.S. Cl.
CPC ............ A61K 47/34 (2013.01); A61K 9/0019 (2013.01); A61K 31/341 (2013.01); A61K 31/519 (2013.01); A61K 9/06 (2013.01); A61K 51/1213 (2013.01)

(58) Field of Classification Search
None
See application file for complete search history.

(56) References Cited

U.S. PATENT DOCUMENTS

| 4,530,840 A | 7/1985 | Tice et al. |
| 4,622,219 A | 11/1986 | Haynes |
| 4,725,442 A | 2/1988 | Haynes |
| 4,767,628 A | 8/1988 | Hutchinson |
| 4,891,225 A | 1/1990 | Langer |
| 4,906,474 A | 3/1990 | Langer |
| 4,938,763 A | 7/1990 | Dunn et al. |
| 4,957,744 A | 9/1990 | Della Valle et al. |
| 5,149,543 A | 9/1992 | Cohen et al. |
| 5,534,269 A | 7/1996 | Igari et al. |
| 5,643,605 A | 7/1997 | Cleland et al. |
| 5,747,058 A | 5/1998 | Tipton et al. |
| 5,871,778 A * | 2/1999 | Kino ................ A61K 9/1647 424/426 |
| 5,968,542 A | 10/1999 | Tipton |
| 6,130,200 A | 10/2000 | Brodbeck et al. |
| 6,291,013 B1 | 9/2001 | Gibson et al. |
| 6,331,311 B1 | 12/2001 | Brodbeck et al. |
| 6,413,536 B1 | 7/2002 | Gibson et al. |
| 6,468,961 B1 | 10/2002 | Brodbeck et al. |
| 6,673,767 B1 | 1/2004 | Brodbeck et al. |
| 6,956,059 B2 | 10/2005 | Coupland |
| 7,820,202 B2 | 10/2010 | Bodmeier |
| 7,833,543 B2 | 11/2010 | Gibson et al. |
| 7,927,618 B2 | 4/2011 | Bodmeier |
| 8,133,507 B2 | 3/2012 | Yum et al. |
| 2002/0064547 A1 | 5/2002 | Chern et al. |
| 2003/0009145 A1 | 1/2003 | Struijker-Boudier et al. |
| 2004/0018238 A1 | 1/2004 | Shukla |
| 2004/0101557 A1 | 5/2004 | Gibson et al. |
| 2004/0258731 A1 | 12/2004 | Hayashi et al. |
| 2007/0077304 A1 | 4/2007 | Luk et al. |
| 2007/0108405 A1 | 5/2007 | Khoo et al. |
| 2007/0196416 A1 | 8/2007 | Chien et al. |
| 2008/0287464 A1 | 11/2008 | Wright et al. |
| 2010/0266655 A1 | 10/2010 | Dadey |
| 2010/0292195 A1 | 11/2010 | Dadey |
| 2013/0171202 A1 | 7/2013 | Gutierro et al. |

(Continued)

FOREIGN PATENT DOCUMENTS

| EP | 0998917 | 5/2000 |
| EP | 1210942 | 6/2002 |

(Continued)

OTHER PUBLICATIONS

U.S. Appl. No. 14/658,072, filed Mar. 13, 2015, Yum, et al.
Berge, L., et al., "Pharmaceutical Salts", *J. of Pharmaceut. Sci.*, vol. 66:1 Jan. 1977 pp. 1-19.
Carraway KM, Meador SK, Sullivan SA, Gibson JW, Tipton AJ, Drug release from a controlled release aerosol: Effects of formulation variables Southern Biosystems, Inc., Birmingham, ALAAPS Indianapolis Nov. 2000.
Communication of a Notice of Opposition, Notice of Opposition and Opponents Grounds of Opposition, from EP 2361609, mailed May 7, 2014.
Desai, et al., "Surface modification of polymer biomaterials for reduced thrombogenicity", *Polym. Mater. Sci. Eng.* 63:731-735, 1991.
Dong, et al., "Development of injectable biodegradable in-situ forming gel implants", *Progress in Pharmaceutical Sciences*, 31:109-113. 2007.

(Continued)

Primary Examiner — James Rogers
(74) Attorney, Agent, or Firm — Greenblum & Bernstein, P.L.C.

(57) ABSTRACT

An injectable depot formulation includes a biocompatible polymer, an organic solvent combined with the biocompatible polymer to form a viscous gel, and a small molecule drug incorporated in the viscous gel such that the formulation exhibits an in vivo release profile having $C_{max}$ to $C_{min}$ ratio less than 200 and lag time less than 0.2.

17 Claims, 2 Drawing Sheets

(56) References Cited

U.S. PATENT DOCUMENTS

| | | |
|---|---|---|
| 2013/0289053 A1 | 10/2013 | Wright et al. |
| 2014/0308352 A1 | 10/2014 | Wright et al. |

FOREIGN PATENT DOCUMENTS

| | | |
|---|---|---|
| EP | 1649850 | 4/2006 |
| EP | 1317254 | 2/2007 |
| EP | 1248596 | 3/2007 |
| EP | 2529756 | 12/2012 |
| EP | 2361609 | 7/2013 |
| GB | 2165148 | 4/1986 |
| JP | S61-37725 | 2/1986 |
| JP | H04-056736 | 5/1992 |
| JP | H05-078364 | 3/1993 |
| JP | H09-315957 | 12/1997 |
| JP | 2001-509146 | 7/2001 |
| JP | 2001-516728 | 10/2001 |
| JP | 2003-063954 | 3/2003 |
| JP | 2004-511431 | 4/2004 |
| WO | 98/27963 | 6/1998 |
| WO | 99/13913 | 5/1999 |
| WO | 00/24374 | 5/2000 |
| WO | 02/00137 | 1/2002 |
| WO | 02/08351 | 1/2002 |
| WO | 02/067895 | 9/2002 |
| WO | 02/076344 | 10/2002 |
| WO | 03/041684 | 5/2003 |
| WO | 03/041685 | 5/2003 |
| WO | 03/041757 | 5/2003 |
| WO | 2004/000269 | 12/2003 |
| WO | 2004/000395 | 12/2003 |
| WO | 2004/011054 | 2/2004 |
| WO | 2004/011065 | 2/2004 |
| WO | 2004/032980 | 4/2004 |
| WO | 2004/043432 | 5/2004 |
| WO | 2004/026357 | 9/2004 |
| WO | 2005/048989 | 6/2005 |
| WO | 2005/070332 | 8/2005 |
| WO | 2005/089670 | 9/2005 |
| WO | 2005/115346 | 12/2005 |
| WO | 2007/084460 | 1/2007 |
| WO | 2008/124013 | 10/2008 |
| WO | 2009/100222 | 2/2009 |
| WO | 2011/151355 | 12/2011 |
| WO | 2011/151356 | 12/2011 |
| WO | 2012/074883 | 6/2012 |
| WO | 2014/164754 | 10/2014 |

OTHER PUBLICATIONS

Eliaz, et al., "Characterization of a polymeric PLGA-injectable implant delivery system for the controlled release of proteins", *J Biomed Mater. Res.* 2000, 50:388-396.
Erickson NM, Kines PP, Meador SK, Middleton JC, Williams CT, Williams JC, "An in vitro degradation study comparing poly(DL-lactide co-glycolide) with acid end groups and ester end groups", 20th Southern Biomedical Engineering Conference 2001.
English language translation of Office Action dated Jun. 15, 2012, from Japanese Application No. 2008-533726.
English Language translation of Japanese Office Action of Apr. 14, 2015 for JP2013-002422.
Gomeni, R., et al., "A model-based approach to characterize the population pharmacokinetics and the relationship between the pharmacokinetic and safety profiles of RBP-7000, a new, long-acting, sustained-release formulation of Risperidone", *J. Clin. Pharmaco.* 58(10) 1010-1019 2013.
Hatefi, et al., "Biodegradable injectable in situ forming drug delivery system", *J. of Contr. Rel.* vol. 80, Jan. 1, 2002, pp. 9-28.
Hou H, etal., *China Med. Press* pp. 223-226, 2011.
Johnson CA, Thompson DL, Jr., Sullivan SA, Gibson JW, Tipton AJ, Simon BW, Burns PJ, "Biodegradable delivery systems for Estradiol: Comparison between Poly (DL-lactide) microspheres and the SABER delivery system", *Proceed Int'l. Symp. Control. Rel. Bioact. Mater.*, 26 (1999), Controlled Release Society, Inc.
Kulkarni RK, et al., "Polylactic acid for surgical implants", *Arch. Surg.* vol. 93, Nov. 1966, 839-843.
Laffont, C., et al., "Population pharmacokinetic modeling and simulation to guide dose selection for RBP-7000, a new sustained-release formulation for Risperidone", *J. Clin. Pharma.* 55(1) 93-103 2014.
Laffont, C., et al., "Population pharmacokinetics and prediction of dopamine D2 Receptor occupancy after multiple doses of RBP-7000, a new sustained-release formulation of risperidone, in schizophrenia patients on stable oral risperidone treatment", *Clin. Pharmacokinetics*, 53:533-543 2014.
Lambert et al., Journal of Controlled Release, 1995 33:189-195.
Lin, at al., Á novel risperidone-loaded SAIB-PLGA mixture matrix depot with a reduced burst release: effect of solvents and PLGA on drug release behaviors in vitro/in vivo, *J. Mater. Sci.: Mater. Med.* (2012) 23:443-455.
Lu, Y., et al., "Sucrose Acetate Isobutyrate as an in situ forming system for sustained riperidone release", *J. Pharm. Sci.*, vol. 96, No. 12, Dec. 2007, 3252-3262.
Lu, Y., et al., "In vivo evaluation of risperidone-SAIB in situ system as a sustained release delivery system in rats", *Eur. J. Pharma and Biopharm.*, 68 (2007) 422-429.
Middleton, et al., Medical Device and Diagnostic Industry News Products and Suppliers 1998.
Middleton JC, Yarbrough JC, "The effect of PEG end groups on the degradation of a 75/25 poly(DL-Iactide-co-glycolide", *Society for Biomaterials* 1999.
Okumu FW, Daugherty A, Dao LN, Fielder PJ, Brooks D, Sane S, Sullivan SA, Tipton AJ, Cleland JL, "Evaluation of the SABER TM delivery system for sustained release of growth hormone formulation design and in vivo assessment" 2001.
Okumu FW, Daugherty A, Sullivan SA, Tipton AJ, Cleland JL, "Evaluation of SABER TM as a local delivery system for rh VEGF-formulation design and in vitro assessment", 2000.
Okumu FW, Dao Le, Fielder PJ, Dybdal N, Brooks D, Sane S, Cleland JL, "Sustained delivery of human growth hormone from a novel gel system: SABER TM", *Biomaterials* 23 (2002) 4353-4358.
Opponent written submissions in patent No. EP2361609 dated Sep. 10, 2015 pp. 1-6.
Opposition Minutes and Opinion in patent No. EP2361609 dated Nov. 27, 2015 pp. 1-20.
Patent owner's written submissions in patent No. EP2361609 dated Sep. 10, 2015 pp. 1-9.
Patent owner's Experimental Report in patent No. EP2361609 dated Aug. 18, 2015.
Summons to Oral Proceedings from European Patent Office in Opposition against EP Patent No. 2361609 dated Feb. 16, 2015. pp. 1-6.
Patent owner's Written Submission in opposition against EP2361609 dated Nov. 19, 2014. pp. 1-10.
Penco M, et al., "A new chain extension reaction on poly(lactic-glycolic acid) (PLGA) thermal oligomers leading to high molecular weight PLGA-based polymeric products," *Polymer International*, 46:203-216, 1998.
Ravivarapu, et al., Journal of Pharmaceutical Sciences 89:732-741.
Shakeel, F., et al., "Solubility of antipsychotic drug risperidone in Transcutol + water co-solvent mixtures at 298.15 to 333.15 K", *J. of Molec. Liq.* 191 (2014) 68-72.
Sinha & Trehan, "Biodegradable Microspheres for Parenteral Delivery", *Critical Reviews in Therapeutic Drug Carrier Systems*, 22(6): 535-602 (2005).
Smith DA, Tipton AJ, "A novel parenteral delivery system", AAPS-Presentation TDD 7270 Annual Meeting, Seattle, WA (1996).
Sullivan SA, Yarbrough JC, Fengl RW, Tipton AJ, Gibson JW, "Sustained release of orally administered active using SABER TM delivery system incorporated into soft gelatin capsules", *Proceed. Int'l. Symo. Control. Rel. Bioact. Mater.*, 25 (1998), Controlled Release Society, Inc.
Sullivan SA, Meador SK, Carraway KM, Williams JC, Gibson JW, Tipton AJ, "Sustained release of lysozyme from the SABER delivery system", AAPS New Orleans, LA 1999.

(56) References Cited

OTHER PUBLICATIONS

Sullivan SA, Meador SK, Dodson KM, Williams JC, Gibson JW, Tipton AJ, "Sustained release of lysozyme from the SABER delivery system", Poster, Southern Biosystems, Inc. Birmingham AL AAPS New Orleans, LA 1999.

Sullivan SA, Meador SK, Dodson KM, Tipton AJ, Gibson JW, "Incorporation of polymer microparticles into sucrose acetate isobutyrate reduces burst and extends release", *Proceed. Int'l. Symp. Control. Rel. Bioact. Mater.*, 27, Controlled Release Society, Inc. (2000).

Tipton AJ, "Sucrose Acetate Isobutyrate (SAIB) for Parenteral Delivery", Reprinted from Modified-Release Drug Delivery Technology, Rathbone, Hadgraft, Roberts (Eds.), 2002 Marcel Dekker, Inc.

Wang, et al., "Synthesis, characterization, biodegration, and drug delivery application of biodegradable lactic/glycolic acid polymers: I. Synthesis and characterization," *J. Biomater. Sci Polymer Edn*, vol. 11, No. 3, pp. 301-318 (2000).

Written Opinion of the International Searching Authority for International Application No. PCT/US2014/023397 dated Sep. 15, 2015.

Yapar, E., et al., "Injectable In Situ forming microparticles: A novel drug delivery system", *Tropical J. of Pharmaceut. Research*, 11(2) 307-318, Apr. 2012.

http://www.absorbables.com/technical/inherent_viscosity.html, published online 2013.

"Relday: First once-monthly subcutaneous risperidone for the management of schizophrenia," partnering overview, 2013.

\* cited by examiner

SUSTAINED RELEASE SMALL MOLECULE DRUG FORMULATION

CROSS REFERENCE TO RELATED APPLICATIONS

This application is a Continuation of application Ser. No. 13/790,930 filed Mar. 8, 2013, which is a Continuation application Ser. No. 11/535,398, filed Sep. 26, 2006, which claims benefit of provisional Application No. 60/722,845, filed Sep. 30, 2005. The disclosures of application Ser. Nos. 13/790,930 and 11/535,398 are expressly incorporated by reference herein in their entireties.

BACKGROUND OF THE INVENTION

The invention relates generally to delivery of small molecule drugs.

The term "small molecule drug," as used herein, refers to beneficial agents having low molecular weight. The beneficial agents are usually synthesized by organic chemistry, but may also be isolated from natural sources such as plants, fungi, and microbes. The common routes for delivering small molecule drugs are oral, injection, pulmonary, and transdermal.

Many psychotherapeutic drugs are small molecule drugs and are usually provided as oral pills or bolus injections that can be administered one or more times daily. However, oral pills and bolus injections may not be optimal routes for administering small molecule psychotherapeutic drugs because of the peaks and troughs observed in plasma concentration after dosing. Adverse effects and loss of therapeutic effect have been associated with plasma concentration peaks and troughs, respectively.

From the foregoing, psychotherapy as well as other forms of therapy presently relying on small molecule drugs administered in the form of oral pills and bolus injections may benefit from a sustained release dosage form designed to minimize variations in plasma concentration following dosing. Administration of psychotherapeutic agents as sustained release formulations will also increase patient compliance.

BRIEF SUMMARY OF THE INVENTION

In one aspect, the invention relates to an injectable depot formulation which comprises a biocompatible polymer, an organic solvent combined with the biocompatible polymer to form a viscous gel, and a small molecule drug incorporated in the viscous gel such that the formulation exhibits an in vivo release profile having $C_{max}$ to $C_{min}$ ratio less than 200 and lag time less than 0.2.

In another aspect, the invention relates to a method of administering a small molecule drug to a subject in a controlled manner which comprises implanting in the subject an effective amount of an injectable depot formulation comprising a biocompatible polymer, an organic solvent combined with the biocompatible polymer to form a viscous gel, and a small molecule drug incorporated in the viscous gel such that the formulation exhibits an in vivo release profile having $C_{max}$ to $C_{min}$ ratio less than 200 and lag time less than 0.2.

Other features and advantages of the invention will be apparent from the following description.

DETAILED DESCRIPTION OF THE INVENTION

Figure 1:
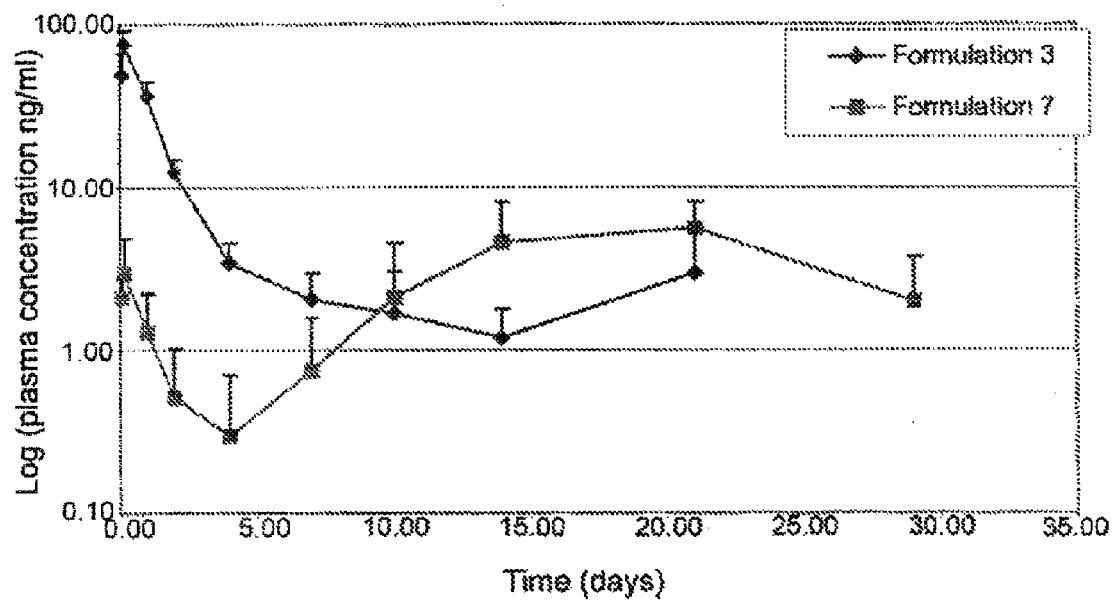
FIG. 1 shows influence of drug salt form on in vivo release profile of formulations according to embodiments of the invention.

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

The invention is based in part on the discovery that incorporation of a sparingly soluble small molecule drug in a depot gel vehicle produces a small molecule drug formulation that has near zero-order release in vivo. The release profile shows minimal lag time and burst. For a depot formulation, this release profile is surprising because the prevailing thought in the art is that a low burst, near zero-order release is virtually impossible to attain unless special steps are taken, such as coatings for drugs and microencapsulation. Several small drug formulations have been identified in this invention with in vivo release profiles having a $C_{max}$ to $C_{min}$ ratio less than 200 and lag time, $T_{lag}$, less than 0.2.

The variable "$C_{min}$" is the minimum drug concentration in plasma or serum. The variable "$C_{max}$" is the maximum drug concentration in plasma or serum. The variable "$T_{lag}$" is the ratio of $T_{valley}$ to $T_{total}$, where $T_{valley}$ is less than $T_{total}$. The variable "$T_{valley}$" is the time to reach $C_{valley}$. The variable "$C_{valley}$" is the first trough of drug concentration in plasma or serum during release. The variable "$T_{total}$" is the total release duration.

Small molecule drug formulations according to embodiments of the invention can be prepared as depot injections. The environment of use is a fluid environment and may include a subcutaneous, intramuscular, intramyocardial, adventitial, intratumoral, or intracerebral portion, a wound site, or tight joint spaces or body cavity of a human or animal. Multiple or repeated injections may be administered to the subject, for example, when the therapeutic effect of the drug has subsided or the period of time for the drug to have a therapeutic effect has lapsed or when the subject requires further administration of the drug for any reason. The formulation serves as an implanted sustained release drug delivery system after injection into the subject. Such controlled release can be over a period of one week, more than one week, one month, or more than one month. Preferably, the controlled release is over at least a period of one week, more preferably over a period of at least one month.

A small molecule drug formulation according to an embodiment of the invention includes a depot gel vehicle. The depot gel vehicle includes a biocompatible polymer, i.e., a polymer that would not cause irritation or necrosis in the environment of use. Biocompatible polymers that may be useful in the invention may be bioerodible, i.e., gradually decompose, dissolve, hydrolyze and/or erode in situ. Examples of bioerodible polymers include, but are not limited to, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, terpolymers and mixtures thereof. The polymer is typically present in the depot gel vehicle in an amount ranging from about 5 to 80% by weight, preferably from about 20 to 70%, often from about 40 to 60% by weight.

In one embodiment, the polymer is a polylactide. A polylactide polymer is a polymer based on lactic acid or a copolymer based on lactic acid and glycolic acid. The polylactide polymer can include small amounts of other comonomers that do not substantially affect the advantageous results that can be achieved in accordance with the invention. The term "lactic acid" includes the isomers L-lactic acid, D-lactic acid, DL-lactic acid, and lactide. The term "glycolic acid" includes glycolide. The polymer may have a lactic-acid to glycolic-acid monomer ratio of from about 100:0 to 15:85, preferably from about 60:40 to 75:25, often about 50:50. The polylactide polymer has a number average molecular weight ranging from about 1,000 to about 120,000, preferably from about 5,000 to about 30,000, as determined by gel permeation chromatography. Suitable polylactide polymers are available commercially.

The depot gel vehicle further includes a biocompatible solvent which when combined with the polymer forms a viscous gel, typically exhibiting viscosity in a range from 500 poise to 200,000 poise, preferably from about 1,000 poise to 50,000 poise. The solvent used in the depot gel vehicle is typically an organic solvent and may be a single solvent or a mixture of solvents. To limit water intake by the depot gel vehicle in the environment of use, the solvent, or at least one of the components of the solvent in the case of a multi-component solvent, preferably has limited miscibility with water, e.g., less than 7% by weight, preferably less than 5% by weight, more preferably less than 3% by weight miscibility with water. Examples of suitable solvents include, but are not limited to, benzyl benzoate (BB), benzyl alcohol (BA), ethyl benzoate (EB), triacetin, and N-methyl-2-pyrrolidone (NMP). The solvent is typically present in the depot gel vehicle in an amount ranging from about 20 to 95% by weight, preferably in an amount ranging from about 30 to 80% by weight, often in an amount ranging from about 40 to 60% by weight.

A formulation according to an embodiment of the invention includes a small molecule drug dispersed or dissolved in a depot gel vehicle as described above. The term "dispersed or dissolved" is intended to encompass all means of establishing the presence of the small molecule drug in the viscous gel and includes dissolution, dispersion, suspension, and the like. Small molecule drugs used in formulations of the invention are sparingly soluble in water. In a preferred embodiment, small molecule drugs used in formulations of the invention have less than 1 mg/ml solubility in water. In one embodiment, small molecule drugs used in formulations of the invention have a molecular weight in a range from 200 to 2,000 Daltons. Small molecule drugs used in formulations of the invention may have a narrow or wide therapeutic window. However, the invention generally delivers salubrious results in terms of $C_{max}$ and toxicity control for small molecule drugs having a narrow therapeutic window. The small molecule drug is typically present in the formulation in an amount ranging from about 1 to 50% by weight, more preferably in an amount ranging from about 5 to 40% by weight, often in an amount ranging from about 10 to 30% by weight.

In one embodiment, a small molecule drug formulation includes a small molecule psychotherapeutic drug, such as a small molecule antipsychotic, dopamine receptor agonist, dopamine receptor antagonist, serotonin receptor agonist, serotonin receptor antagonist, and serotonin uptake inhibitor drug. Table 1 below shows physiochemical properties of some small molecule psychotherapeutic drugs. R209130-base has the molecular formula $C_{19}H_{20}FNO$. R209130-mandelic acid salt (R209130) has the molecular formula $C_{19}H_{20}FNO.C_8H_8O_3$. R209130-tartaric acid salt (R167154) has the molecular formula $C_{19}H_{20}FNO.C_4H_6O_6$. R209130 and its analogs possess putative atypical antipsychotic properties and have demonstrated antianxiety, antidepressive, and socializing effects in animal models. These characteristics may be attributed to R209130 dual antagonism of central dopamine $D_2$ receptors, serotonin 5-$HT_{2A}$ and 5-$HT_{2C}$ receptors, and the inhibition norepinephrine uptake. Risperidone-base has the molecular formula $C_{23}H_{27}FN_4O_2$.

Risperidone-pamoate has the molecular formula $C_{23}H_{27}FN_4O_2 \cdot C_{23}H_{16}O_6$. Risperidone is a combined serotonin (5-HT$_2$) and dopamine (D2) receptor antagonist.

TABLE 1

| Property | R209130 | R167154 | R209130 base | Risperidone base | Risperidone pamoate |
|---|---|---|---|---|---|
| pKa | 9.2 | 9.2 | 9.2 | 8.2/3.1 | 8.2/3.1 |
| Solubility in H$_2$O (mg/ml) | 0.32 (pH 4.9) | 41.84 (pH 3.4) | 0.008 (pH 9.5) | 0.09 (pH 8.8) | 0.2 (pH 7.2) |
| Solubility at pH 7 (mg/ml) | 0.35 | 6.1 (pH 6.5) | 2 | 1 | 0.2 (pH 7.2) |
| Solubility in BB (µg/ml) | 58.6 at 40° C. | 10.3 at 40° C. | >200,000 | 32,000 | 50 |
| Solubility in BA (mg/ml) | 7.3 at 40° C. | 41.3 at 40° C. | >200,000 | 407 | 2.97 |
| Intrinsic dissolution rate (mg/cm$^2 \cdot$ min) | 0.054 | 3.7 | 0.7 | 0.0025 | N/A |
| LogP (C$_8$OH/pH 7 buffer) | 3.9 | 4.0 | N/A | 3.04 | N/A |
| Molecular weight | 449.5 | 447.5 | 297.4 | 410.5 | 798.5 |

A study was conducted to determine the PK profile of a small molecule drug delivered from a depot gel vehicle according to the invention and the influence of salt form of the drug, solvent type, polymer type, polymer molecular weight, polymer/solvent ratio, drug loading, and particle size on the PK profile.

The following examples are presented for illustration purposes and are not intended to limit the invention as otherwise described herein.

Example 1

A depot gel vehicle was prepared as follows: A HDPE container was tared on a Mettler PJ3000 top loader balance. Poly D,L-lactide-co-glycolide (PLGA), (L/G ratio of 50/50), available as RESOMER® RG 502 (PLGA-502), was weighed into the container. The container containing PLGA-502 was tared, and the corresponding solvent was added to the PLGA-502. Amounts expressed as percentages for various combinations of PLGA-502 and solvent are set forth below in Table 2. A hybrid mixer was used to mix the PLGA-502 and solvent mixture, resulting in a clear gel-like solution of the polymer in the solvent.

TABLE 2

| Formulation | PLGA-502 (wt %, g) | Benzyl Benzoate (wt %, g) | Benzyl Alcohol (wt %, g) |
|---|---|---|---|
| A | 50.067 | 50.044 | |
| B | 50.023 | 24.988 | 24.988 |
| C | 50.365 | 45.093 | 5.1780 |
| D | 50.139 | 37.553 | 12.560 |
| E | 50.350 | 45.193 | |

Additional depot gel vehicles were prepared with solvents, selected from benzyl benzoate (BB), benzyl alcohol (BA), ethyl benzoate (EB), ethyl hydroxide (EtOH), triacetin, and N-methyl-2-pyrrolidone (NMP), and mixtures thereof, and polymers, selected from Poly D,L-lactide, available as RESOMER® L 104, RESOMER® R 104, RESOMER® 202, RESOMER® 203, RESOMER® 206, RESOMER® 207, RESOMER® 208; PLGA, L/G ratio of 50/50, available as RESOMER® RG 502H; PLGA, L/G ratio of 50/50, available as RESOMER® RG 503; PLGA, UG ratio of 50/50, available as RESOMER® RG 755; Poly L-lactide, molecular weight of 2000, available as RESOMER® L 206, RESOMER® L 207, RESOMER® L 209, RESOMER® L 214; Poly L-lactide-co-D,L-lactide, L/G ratio of 90/10, available as RESOMER® LR 209; PLGA, UG ratio of 75/25, available as RESOMER® RG 752, RESOMER® RG 756, PLGA, L/G ratio of 85/15, available as RESOMER® RG 858; Poly L-lactide-co-trimethylene carbonate, L/G ratio of 70/30, available as RESOMER® LT 706, and Poly dioxanone, available as RESOMER® X210 (Boehringer Ingelheim Chemicals, Inc. Petersburg, Va.); DL-lactide/glycolide (DL), L/G ratio of 100/0, available as MEDISORB® Polymer 100 DL High, MEDISORB® Polymer 100 DL Low; DL-lactide/glycolide (DL), L/G ratio of 85/15, available as MEDISORB® Polymer 8515 DL High, MEDISORB® Polymer 8515 DL Low; DL-lactide/glycolide (DL), L/G ratio of 75/25, available as MEDISORB® Polymer 7525 DL High, MEDISORB® Polymer 7525 DL Low; DL-lactide/glycolide (DL), L/G ratio of 65/35, available as MEDISORB® Polymer 6535 DL High, MEDISORB® Polymer 6535 DL Low; DL-lactide/glycolide (DL), L/G ratio of 54/46, available as MEDISORB® Polymer 5050 DL High, MEDISORB® Polymer 5050 DL Low, MEDISORB® 5050 Polymer DL 2A(3), MEDISORB® 5050 Polymer DL 3A(3), MEDISORB® 5050 Polymer DL 4A(3) (Medisorb Technologies International L.P., Cincinnati, Ohio); and PLGA (L/G ratio of 50/50), PLGA (L/G ratio of 65/35), PLGA (L/G ratio of 75/25), PLGA (L/G ratio of 85/15), Poly D,L-lactide, Poly L-lactide, Poly glycolide, Poly ε-caprolactone, Poly D,L-lactide-co-caprolactone (L/C ratio of 25/75), and Poly D,L-lactide-co-caprolactone (L/C ratio of 75/25), available from Birmingham Polymers, Inc., Birmingham, Ala. Polycaprolactone-glycolic acid-lactic acid copolymer (PCL-GA-LA) was also used either mixed with polyvinylpyrrolidone (PVP) or by itself. Typical molecular weights of these polymers are in the range of 6,000 to 20,000.

Example 2

Drug particles were prepared as follows: R209130, R167154, risperidone base, or risperidone pamoate drug was passed through sieves of different sizes to obtain drug particles having a certain range of particle size distribution. Particles in the range of 20 to 63 µm, 63 to 125 µm, 75 to 125 µm, or less than 38 µm were obtained. Micronized particles received were also used as drug particles.

Example 3

Depot formulations were prepared as follows: sieved drug particles prepared as described in Example 2 were added into the depot gel vehicles prepared as described in Example 1 in an amount of 0 to 50% by weight and blended manually until the drug particles were wetted completely. Then, the mixture of drug particles and depot gel was thoroughly blended by conventional mixing using a Caframo mechanical stirrer with an attached square-tip metal spatula. Final homogeneous gel formulations were transferred to 3, 10, or 30 cc disposable syringes for storage or dispensing.

Example 4

A representative number of implantable gels were prepared in accordance with the foregoing procedures and tested in vivo in rats to determine release of the drug as determined by blood serum or plasma concentration of drug as a function of time.

In general, in vivo studies in rats were performed following an open protocol to determine plasma levels of the drug (e.g., R209130, R167154, risperidone base, risperidone pamoate) upon systemic administration of the drug via the implant systems of the invention. Depot gel formulations containing the drug, prepared as described in the Examples above, were loaded into 0.5 cc disposable syringes. Disposable needles (18 gauge) were attached to the syringes and heated to 37° C. using a circulator bath. The depot gel formulations were injected into rats. Blood was drawn at specified time intervals and analyzed for drug content. All plasma samples were stored at 4° C. prior to analysis.

Example 5

This example investigates influence of drug salt form on in vivo release of small molecule drugs from depot gel vehicles.

Particles of R209130 and R167154, in appropriate size range, were incorporated in depot gel vehicles, as per procedure in Example 3. Resulting formulations are illustrated in Table 2 below. Final homogeneous depot formulations were transferred to 3, 10, or 30 cc disposable syringes for storage or dispensing. In vivo release of the drugs were analyzed, as per procedure in Example 4. In vivo release profiles of the formulations are shown in FIG. 1. $C_{max}$ to $C_{min}$ ratio and $T_{lag}$ of the formulations are shown in Table 2. R167154 and R209130 are different salt forms of the same drug. Formulation 7 (R209130) has $C_{max}$ to $C_{min}$ ratio of 19.2 and $T_{lag}$ of 0.61, while formulation 3 (R167154) has $C_{max}$ to $C_{min}$ ratio of 25.7 and $T_{lag}$ of 0.33. This example shows that in vivo release is influenced by salt form of the formulation. Even though $T_{lag}$ for formulation 7 (R209130) is higher than $T_{lag}$ for formulation 3 (R167154), formulation 7 appears to have better release rate profile and duration of release in comparison to formulation 3.

TABLE 2

| No. | PLGA (wt %) | BA (wt %) | BB (wt %) | Triacetin (wt %) | Drug (wt %) | $C_{max}/C_{min}$ | $T_{lag}$ |
|---|---|---|---|---|---|---|---|
| $3^{2,a,II,\alpha,A}$ | 45 | 22.5 | 22.5 | 0 | 10 | 25.7 | 0.33 |
| $7^{1,a,II,\alpha,B}$ | 45 | 22.5 | 22.5 | 0 | 10 | 19.2 | 0.61 |

[1] = R209130,
[2] = R167154,
[3] = risperidone base,
[4] = risperidone pamoate;
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 µm,
[B] = 20-63 µm,
[C] = 75-125 µm,
[D] = <38 µm,
[E] = micronized,
[F] = as is,
[G] = not applicable;
NV = no valley Example 6

This example investigates influence of solvent type on in vivo release of small molecule drugs from depot gel vehicles.

Figure 2:
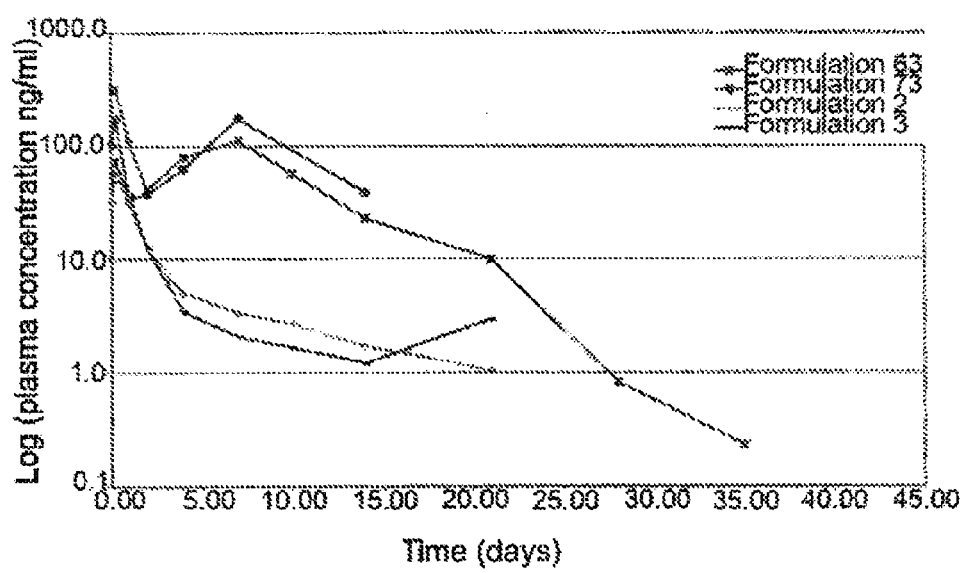
FIG. 2 shows influence of solvent type on in vivo release profile of formulations according to embodiments of the invention.

Depot gel vehicles were prepared with PLGA-502 and a solvent selected from BA, BB, EB, EtOH, NMP, and triacetin, and combinations thereof, as per procedure in Example 1. The depot gel vehicles were loaded with drug substance, in appropriate range, as per procedure in Example 3. Resulting formulations are illustrated in Table 3 below. Final homogeneous depot formulations were transferred to 3, 10 or 30 cc disposable syringes for storage or dispensing. In vivo release profiles of the formulations in Table 3 are shown in FIG. 2. $C_{max}$ to $C_{min}$ ratio and $T_{lag}$ of the formulations are shown in Table 3.

TABLE 3

| | Target content in formulation (% w/w) | | | | | | | $C_{max}/C_{min}$ | $T_{lag}$ |
|---|---|---|---|---|---|---|---|---|---|
| No. | PLGA | BA | BB | EtOH | NMP | Triacetin | EB | Drug | |
| $2^{2,a,II,\alpha,A}$ | 45 | 0 | 45 | 0 | 0 | 0 | 0 | 10 | 59.86 | NV |
| $3^{2,a,II,\alpha,A}$ | 45 | 22.5 | 22.5 | 0 | 0 | 0 | 0 | 10 | 25.68 | 0.33 |
| $10^{1,a,III,\alpha,C}$ | 40 | 40 | 0 | 0 | 0 | 0 | 0 | 20 | 4.35 | 0.61 |
| $14^{1,a,III,\alpha,C}$ | 40 | 20 | 20 | 0 | 0 | 0 | 0 | 20 | 3.15 | 0.50 |

TABLE 3-continued

| | Target content in formulation (% w/w) | | | | | | | | $C_{max}/$ | |
|---|---|---|---|---|---|---|---|---|---|---|
| No. | PLGA | BA | BB | EtOH | NMP | Triacetin | EB | Drug | $C_{min}$ | $T_{lag}$ |
| 63[3,a,VII,α,C] | 43.3 | 0 | 0 | 0 | 0 | 43.3 | 0 | 13.4 | 1364.43 | 0.14 |
| 73[3,a,VII,α,G] | 43.3 | 0 | 0 | 0 | 0 | 0 | 43.3 | 13.4 | 5.20 | N/A |

[1] = R209130,
[2] = R167154,
[3] = risperidone base,
[4] = risperidone pamoate,
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
NV = no valley In Table 3 above, formulation 63 (risperidone base/PLGA/triacetin depot) has a $C_{max}$ to $C_{min}$ ratio of 1364.64. On the other hand, formulation 73 (risperidone base/PLGA/EB depot) has a $C_{max}$ to $C_{min}$ ratio of 5.20, which is significantly lower than the $C_{max}$ to $C_{min}$ ratio for formulation 63. Formulation 2 (R167154/PLGA/BB depot) has a $C_{max}$ to $C_{min}$ ratio of 59.68. On the other hand, formulation 3 (R167154/PLGA/BA/BB) has a $C_{max}$ to $C_{min}$ ratio of 25.68, which is less than half the $C_{max}$ to $C_{min}$ ratio for formulation 2. This indicates that solvent type can influence in vivo release profile of the formulation.

Example 7

This example investigates influence of polymer type on in vivo release of small molecule drugs from depot gel vehicles.

Figure 3:
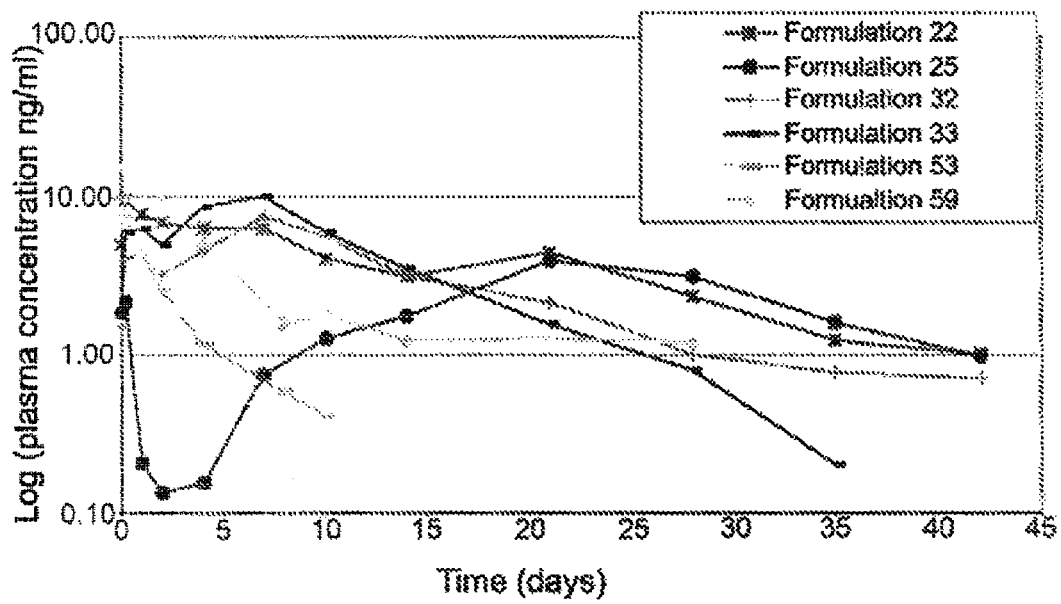
FIG. 3 shows influence of polymer type on in vivo release profile of formulations according to embodiments of the invention.

Depot gel vehicles were prepared with different polymers and loaded with R209130, in appropriate size range, as per procedure in Example 3. Resulting formulations are illustrated in Table 4 below. Final homogeneous depot formulations were transferred to 3, 10 or 30 cc disposable syringes for storage or dispensing. Table 4 shows $C_{max}$ to $C_{min}$ ratio and $T_{lag}$ for in vivo release profiles of the formulations. FIG. 3 shows in vivo release profiles of formulations in Table 4.

TABLE 4

| | Target content in formulation (% w/w) | | | | | |
|---|---|---|---|---|---|---|
| No. | Polymer | BA | BB | Drug | $C_{max}/C_{min}$ | $T_{lag}$ |
| 22[1,a,IV,α,C] | 35 | 35 | 0 | 30 | 9.86 | 0.17 |
| 23[1,a,IV,α,C] | 35 | 0 | 35 | 30 | 6.83 | 0.17 |
| 24[1,a,IV,α,E] | 35 | 0 | 35 | 30 | 44.0 | NV |
| 25[1,c,IV,α,C] | 35 | 0 | 35 | 30 | 29.49 | 0.45 |
| 32[1,d,IV,α,C] | 35 | 0 | 35 | 30 | 10.65 | 0.12 |
| 33[1,f,IV,α,C] | 35 | 0 | 35 | 30 | 6.35 | 0.14 |
| 34[1,a,IV,α,C] | 35 | 35 | 0 | 30 | 8.75 | 0.23 |
| 35[1,c,IV,α,C] | 35 | 0 | 35 | 30 | 44.21 | NV |
| 48[1,c,IV,α,E] | 35 | 0 | 35 | 30 | 163.12 | NV |
| 53[1,e,IV,α,E] | 35 | 0 | 35 | 30 | 31.16 | 0.25 |
| 59[1,d,IV,α,C] | 35 | 0 | 35 | 30 | 6.26 | 0.07 |

[1] = R209130,
[2] = R167154,
[3] = risperidone base,
[4] = risperidone pamoate,
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
NV = no valley Example 8

This example investigates influence of molecular weight of polymers on in vivo release of small molecule drugs from depot gel vehicles.

Depot gel vehicles were prepared with polymers with different molecular weights and loaded with drug substance, in appropriate size range, as per procedure in Example 3. Resulting formulations are illustrated in Table 5 below. Final homogeneous depot formulations were transferred to 3, 10 or 30 cc disposable syringes for storage or dispensing. Table 5 shows $C_{max}$ to $C_{min}$ ratio and $T_{lag}$ for in vivo release profiles of the formulations.

TABLE 5

| No. | Target content in Formulation (% w/w) | | | | | $C_{max}/C_{min}$ | $T_{lag}$ |
|---|---|---|---|---|---|---|---|
| | PLGA | BA | BB | Tri-acetin | Drug | | |
| 10[1,a,III,α,C] | 40 | 40 | 0 | 0 | 20 | 4.35 | 0.61 |
| 11[1,a,III,α,D] | 40 | 40 | 0 | 0 | 20 | 12.06 | 0.61 |
| 12[1,a,IV,α,C] | 35 | 35 | 0 | 0 | 30 | 4.78 | 0.14 |
| 13[1,a,IV,α,D] | 35 | 35 | 0 | 0 | 30 | 5.29 | 0.36 |
| 21[1,c,III,α,C] | 40 | 40 | 0 | 0 | 20 | 48.55 | No valley |
| 25[1,c,IV,α,C] | 35 | 0 | 35 | 0 | 30 | 29.49 | 0.45 |
| 26[1,c,IV,α,D] | 35 | 0 | 35 | 0 | 30 | 41.67 | No valley |
| 48[1,c,IV,α,E] | 35 | 0 | 35 | 0 | 30 | 163.12 | No valley |
| 49[1,c,IV,δ,E] | 42 | 0 | 28 | 0 | 30 | 66.31 | 0.39 |
| 63[3,a,VII,α,C] | 43.3 | 0 | 0 | 43.3 | 13.4 | 1364.43 | 0.14 |
| 64[4,c,VIII,α,C] | 36.9 | 0 | 36.9 | 0 | 26.1 | 11.66 | No valley |
| 69[4,a,VIII,α,E] | 36.9 | 0 | 36.9 | 0 | 26.1 | 14.12 | 0.90 |
| 70[4,c,VIII,α,C] | 36.9 | 0 | 36.9 | 0 | 26.1 | 22.11 | no valley |
| 72[3,a,VII,α,G] | 43.3 | 0 | 43.3 | 0 | 13.4 | 24.48 | N/A |

[1]= R209130,
[2]= R167154,
[3]= risperidone base,
[4]= risperidone pamoate,
[a]= 50/50 PLGA-502 (MW = 16,000),
[b]= 50/50 PLGA-502H (MW = 11,000),
[c]= 50/50 PLGA (MW = 6400),
[d]= 40/55/5 PCL-GA-LA (MW = ~13,500),
[e]= 75/25 PLGA (MW = 14,300),
[f]= 80/20 PCL-GA-LA/PVP,
[g]= RG502:RG502H (1:1);
[α]= P/S ratio of 50/50,
[β]= P/S ratio of 40/60,
[χ]= P/S ratio of 45/55,
[δ]= P/S ratio of 60/40,
[ε]= P/S ratio of 55/45;
[A]= 63-125 μm,
[B]= 20-63 μm,
[C]= 75-125 μm,
[D]= <38 μm,
[E]= micronized,
[F]= as is,
[G]= not applicable;
NV = no valley

Example 9

This example investigates influence of polymer/solvent ratios on in vivo release of small molecule drugs from depot gel vehicles.

Depot gel vehicles were prepared with different polymer/solvent ratios and loaded with drug substance, in appropriate size range, as per procedure in Example 3. Resulting formulations are illustrated in Table 6 below. Final homogeneous depot formulations were transferred to 3, 10 or 30 cc disposable syringes for storage or dispensing. Table 6 shows $C_{max}$ to $C_{min}$ ratio and $T_{lag}$ for in vivo release profiles of the formulations.

TABLE 6

| No. | Target content in Formulation (% w/w) | | | | $C_{max}/C_{min}$ | $T_{lag}$ |
|---|---|---|---|---|---|---|
| | PLGA | BA | BB | EtOH | Drug | | |
| 22[1,a,IV,α,C] | 35 | 0 | 0 | 30 | 9.86 | 0.17 |
| 23[1,a,IV,α,C] | 35 | 35 | 0 | 30 | 6.83 | 0.17 |
| 24[1,a,IV,α,E] | 35 | 35 | 0 | 30 | 44.00 | NV |

TABLE 6-continued

| No. | Target content in Formulation (% w/w) | | | | $C_{max}/C_{min}$ | $T_{lag}$ |
|---|---|---|---|---|---|---|
| | PLGA | BB | EtOH | Drug | | |
| 25[1,c,IV,α,C] | 35 | 35 | 0 | 30 | 29.49 | 0.45 |
| 26[1,c,IV,α,D] | 35 | 35 | 0 | 30 | 41.67 | NV |
| 27[1,c,IV,β,C] | 28 | 42 | 0 | 30 | 54.16 | NV |
| 28[1,c,IV,β,D] | 28 | 42 | 0 | 30 | 120.74 | NV |
| 29[1,a,IV,χ,C] | 31.5 | 34.65 | 3.85 | 30 | 1.93 | NV |
| 30[1,a,IV,χ,D] | 31.5 | 34.65 | 3.85 | 30 | 7.07 | 0.29 |
| 48[1,c,IV,α,E] | 35 | 35 | 0 | 30 | 163.12 | NV |
| 49[1,c,IV,δ,E] | 42 | 28 | 0 | 30 | 66.31 | 0.39 |
| 52[1,e,IV,β,E] | 28 | 42 | 0 | 30 | 47.86 | NV |
| 53[1,e,IV,α,E] | 35 | 35 | 0 | 30 | 31.16 | 0.25 |
| 56[1,b,IV,ε,F] | 38.5 | 31.5 | 0 | 30 | 17.10 | NV |
| 65[4,c,VIII,α,E] | 36.9 | 36.9 | 0 | 26.1 | 50.87 | NV |
| 66[4,c,VIII,ε,G] | 40.6 | 33.2 | 0 | 26.1 | 38.39 | NV |
| 67[4,c,VIII,ε,G] | 33.2 | 40.6 | 0 | 26.1 | 43.55 | NV |

[1]= R209130,
[2]= R167154,
[3]= risperidone base,
[4]= risperidone pamoate,
[a]= 50/50 PLGA-502 (MW = 16,000),
[b]= 50/50 PLGA-502H (MW = 11,000),
c= 50/50 PLGA (MW = 6400),
[d]= 40/55/5 PCL-GA-LA (MW = ~13,500),
[e]= 75/25 PLGA (MW = 14,300),
[f]= 80/20 PCL-GA-LA/PVP,
[g]= RG502:RG502H (1:1);
[α]= P/S ratio of 50/50,
[β]= P/S ratio of 40/60,
[χ]= P/S ratio of 45/55,
[δ]= P/S ratio of 60/40,
[ε]= P/S ratio of 55/45;
[A]= 63-125 μm,
[B]= 20-63 μm,
[C]= 75-125 μm,
[D]= <38 μm,
[E]= micronized,
[F]= as is,
[G]= not applicable;
NV = no valley

Example 10

This example investigates influence of drug loading on in vivo release of small molecule drugs from depot gel vehicles Depot gel vehicles were prepared with varying percentages of drug, in appropriate size range, as per procedure in Example 3. Resulting formulations are illustrated in Table 7 below. Final homogeneous depot formulations were transferred to 3, 10 or 30 cc disposable syringes for storage or dispensing. Table 7 shows $C_{max}$ to $C_{min}$ ratio and $T_{lag}$ for in vivo release profiles of the formulations.

TABLE 7

| Formulation No. | Target content in Formulation (% w/w) | | | | $C_{max}/C_{min}$ | $T_{lag}$ |
|---|---|---|---|---|---|---|
| | PLGA | BA | BB | Drug | | |
| 4[1,a,II,α,B] | 45 | 45 | 0 | 10 | 4.37 | 0.50 |
| 5[1,a,III,α,B] | 40 | 20 | 20 | 20 | 10.66 | 0.61 |
| 7[1,a,II,α,B] | 45 | 22.5 | 22.5 | 10 | 19.17 | 0.61 |
| 10[1,a,III,α,C] | 40 | 40 | 0 | 20 | 4.35 | 0.61 |

TABLE 7-continued

| Formulation No. | Target content in Formulation (% w/w) | | | | $C_{max}/C_{min}$ | $T_{lag}$ |
|---|---|---|---|---|---|---|
| | PLGA | BA | BB | Drug | | |
| 11[1,a,III,α,D] | 40 | 40 | 0 | 20 | 12.06 | 0.61 |
| 12[1,a,IV,α,C] | 35 | 35 | 0 | 30 | 4.78 | 0.14 |
| 13[1,a,IV,α,D] | 35 | 35 | 0 | 30 | 5.29 | 0.36 |
| 14[1,a,III,α,C] | 40 | 20 | 20 | 20 | 3.15 | 0.50 |
| 15[1,a,III,α,D] | 40 | 20 | 20 | 20 | 9.60 | 0.61 |
| 16[1,a,IV,α,C] | 35 | 17.5 | 17.5 | 30 | 7.16 | 0.61 |
| 17[1,a,IV,α,D] | 35 | 17.5 | 17.5 | 30 | 17.35 | 0.36 |
| 18[1,a,V,α,C] | 30 | 30 | 0 | 40 | 3.54 | 0.39 |

[1]= R209130,
[2]= R167154,
[3]= risperidone base,
[4]= risperidone pamoate,
[a]= 50/50 PLGA-502 (MW = 16,000),
[b]= 50/50 PLGA-502H (MW = 11,000),
[c]= 50/50 PLGA (MW = 6400),
[d]= 40/55/5 PCL-GA-LA (MW = ~13,500),
[e]= 75/25 PLGA (MW = 14,300),
[f]= 80/20 PCL-GA-LA/PVP,
[g]= RG502:RG502H (1:1);
[α]= P/S ratio of 50/50,
[β]= P/S ratio of 40/60,
[χ]= P/S ratio of 45/55,
[δ]= P/S ratio of 60/40,
[ε]= P/S ratio of 55/45;
[A]= 63-125 μm,
[B]= 20-63 μm,
[C]= 75-125 μm,
[D]= <38 μm,
[E]= micronized,
[F]= as is,
[G]= not applicable;
NV = no valley

Example 11

This example investigates influence of drug particle size on in vivo release of small molecule drugs from depot gel vehicles.

Depot gel vehicles were prepared and loaded with drug particles in appropriate size range, as per procedure in Example 3. Resulting formulations are illustrated in Table 8 below. Final homogeneous depot formulations were transferred to 3, 10 or 30 cc disposable syringes for storage or dispensing. Table 8 shows $C_{max}$ to $C_{min}$ ratio and $T_{lag}$ for in vivo release profiles of the formulations.

TABLE 8

| Formulation No. | Target content in Formulation (% w/w) | | | | $C_{max}/C_{min}$ | $T_{lag}$ |
|---|---|---|---|---|---|---|
| | PLGA | BA | BB | Drug | | |
| 7[1,a,II,α,B] | 45 | 22.5 | 22.5 | 10 | 19.17 | 0.61 |
| 10[1,a,III,α,C] | 40 | 40 | 0 | 20 | 4.35 | 0.61 |
| 11[1,a,III,α,D] | 40 | 40 | 0 | 20 | 12.06 | 0.61 |
| 23[1,a,IV,α,C] | 35 | 0 | 35 | 30 | 6.83 | 0.17 |
| 24[1,a,IV,α,E] | 35 | 0 | 35 | 30 | 44.00 | NV |
| 25[1,c,IV,α,C] | 35 | 0 | 35 | 30 | 29.49 | 0.45 |
| 26[1,c,IV,α,D] | 35 | 0 | 35 | 30 | 41.67 | NV |
| 64[4,c,VIII,α,C] | 36.9 | 0 | 36.9 | 26.1 | 11.66 | NV |
| 65[4,c,VIII,α,E] | 36.9 | 0 | 36.9 | 26.1 | 50.87 | NV |
| 66[4,c,VIII,ε,G] | 40.6 | 0 | 33.2 | 26.1 | 38.39 | NV |
| 72[3,a,VII,α,G] | 43.3 | 0 | 43.3 | 13.4 | 24.48 | N/A |

[1]= R209130,
[2]= R167154,
[3]= risperidone base,
[4]= risperidone pamoate,
[a]= 50/50 PLGA-502 (MW = 16,000),
[b]= 50/50 PLGA-502H (MW = 11,000),
[c]= 50/50 PLGA (MW = 6400),
[d]= 40/55/5 PCL-GA-LA (MW = ~13,500),
[e]= 75/25 PLGA (MW = 14,300),
[f]= 80/20 PCL-GA-LA/PVP,
[g]= RG502:RG502H (1:1);
[α]= P/S ratio of 50/50,
[β]= P/S ratio of 40/60,
[χ]= P/S ratio of 45/55,
[δ]= P/S ratio of 60/40,
[ε]= P/S ratio of 55/45;
[A]= 63-125 μm,
[B]= 20-63 μm,
[C]= 75-125 μm,
[D]= <38 μm,
[E]= micronized,
[F]= as is,
[G]= not applicable;
NV = no valley

Example 12

Figure 4:
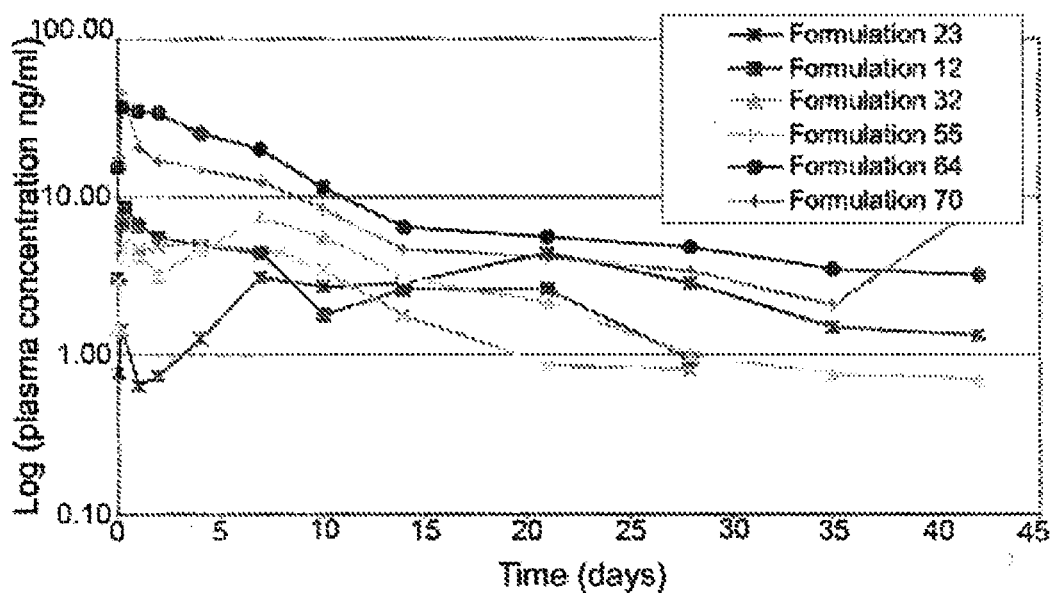
FIG. 4 shows formulations having near zero-order release profiles according to embodiments of the invention.

A formulation is described as near zero-order if the ratio of $C_{max}$ to $C_{min}$ is less than 200, preferably less than 50, more preferably less than 30. $T_{lag}$ in release of formulation is preferably less than 0.2. Formulations that do not show $C_{valley}$ do not exhibit lag. Table 9 shows a number of formulations that exhibited the characteristic near zero-order release. FIG. 4 shows in vivo release profiles of selected formulations in Table 9.

TABLE 9

| Formulation No. | Target content in Formulation (% w/w) | | | | | $C_{max}/C_{min}$ | $T_{lag}$ |
|---|---|---|---|---|---|---|---|
| | Polymer | BA | BB | EtOH | Drug Particles | | |
| 12[1,a,IV,α,C] | 35 | 35 | 0 | 0 | 30 | 4.78 | 0.14 |
| 22[1,a,IV,α,C] | 35 | 35 | 0 | 0 | 30 | 9.86 | 0.17 |
| 23[1,a,IV,α,C] | 35 | 0 | 35 | 0 | 30 | 6.83 | 0.17 |
| 29[1,a,IV,χ,C] | 31.5 | 0 | 34.65 | 3.85 | 30 | 1.93 | NV |
| 32[1,d,IV,α,C] | 35 | 35 | 0 | 0 | 30 | 10.65 | 0.12 |
| 33[1,f,IV,α,C] | 35 | 0 | 35 | 0 | 30 | 6.35 | 0.14 |
| 35[1,c,IV,α,C] | 35 | 0 | 35 | 0 | 30 | 44.21 | NV |
| 55[1,e,IV,α,C] | 35 | 0 | 35 | 0 | 30 | 6.33 | 0.11 |
| 56[1,b,IV,ε,F] | 38.5 | 0 | 31.5 | 0 | 30 | 17.10 | NV |
| 60[1,c,VI,α,C] | 25 | 0 | 25 | 0 | 50 | 12.90 | 0.07 |
| 61[1,c,IV,α,C] | 35 | 0 | 35 | 0 | 30 | 26.53 | 0.11 |

TABLE 9-continued

Target content in Formulation (% w/w)

| Formulation No. | Polymer | BA | BB | EtOH | Drug Particles | $C_{max}/C_{min}$ | $T_{lag}$ |
|---|---|---|---|---|---|---|---|
| 64[4,c,VIII,α,C] | 36.9 | 0 | 36.9 | 0 | 26.1 | 11.66 | NV |
| 70[4,c,VIII,α,C] | 36.9 | 0 | 36.9 | 0 | 26.1 | 22.11 | NV |

[1] = R209130,
[2] = R167154,
[3] = risperidone base,
[4] = risperidone pamoate,
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
NV = no valley While the invention has been described with respect to a limited number of embodiments, those skilled in the art, having benefit of this disclosure, will appreciate that other embodiments can be devised which do not depart from the scope of the invention as disclosed herein.

What is claimed is:

1. A formulation, comprising:
a copolymer of lactic acid and glycolic acid having a number average molecular weight ranging from 1000 Daltons to 120,000 Daltons;
an organic solvent combined with the copolymer to form a viscous gel, the organic solvent being selected from benzyl alcohol, benzyl benzoate, ethyl benzoate, ethyl hydroxide, N-methyl-2-pyrrolidone, and mixtures thereof; and
risperidone base in particle form incorporated in the viscous gel, wherein the particles have an average particle size ranging from 0.1 μm to 125 μm,
wherein the copolymer and the organic solvent comprise a vehicle, the copolymer is present in the vehicle in an amount ranging from 40% to 55% by weight, and the organic solvent is present in the vehicle in an amount ranging from 45% to 60% by weight.

2. The formulation of claim 1, wherein the copolymer of lactic acid and glycolic acid has a monomer ratio of lactic acid to glycolic acid ranging from about 100:0 to 60:40.

3. The formulation of claim 1, wherein the copolymer of lactic acid and glycolic acid has a monomer ratio of lactic acid to glycolic acid ranging from 100:0 to 75:25.

4. The formulation of claim 1, wherein the copolymer has a number average molecular weight ranging from 1000 Daltons to 30,000 Daltons.

5. The formulation of claim 1, wherein the copolymer has a number average molecular weight ranging from 5000 Daltons to 30,000 Daltons.

6. The formulation of claim 1, wherein the organic solvent comprises N-methyl-2-pyrrolidone.

7. The formulation of claim 1, wherein the risperidone base is present in the formulation in an amount ranging from 5 wt % to 40 wt %.

8. The formulation of claim 1, wherein the risperidone base is present in the formulation in an amount ranging from 10 wt % to 30 wt %.

9. The formulation of claim 1, wherein the copolymer of lactic acid and glycolic acid has a monomer ratio of lactic acid to glycolic acid ranging from about 100:0 to 60:40, and the copolymer has a number average molecular weight ranging from 1000 Daltons to 30,000 Daltons.

10. The formulation of claim 1, wherein the copolymer of lactic acid and glycolic acid has a monomer ratio of lactic acid to glycolic acid ranging from 100:0 to 75:25, and the copolymer has a number average molecular weight ranging from 5000 Daltons to 30,000 Daltons.

11. The formulation of claim 1, wherein the copolymer of lactic acid and glycolic acid has a monomer ratio of lactic acid to glycolic acid ranging from about 100:0 to 60:40, the copolymer has a number average molecular weight ranging from 1000 Daltons to 30,000 Daltons, and the organic solvent comprises N-methyl-2-pyrrolidone.

12. The formulation of claim 1, wherein the copolymer of lactic acid and glycolic acid has a monomer ratio of lactic acid to glycolic acid ranging from 100:0 to 75:25, the copolymer has a number average molecular weight ranging from 5000 Daltons to 30,000 Daltons, and the organic solvent comprises N-methyl-2-pyrrolidone.

13. The formulation of claim 1, wherein the organic solvent comprises N-methyl-2-pyrrolidone, and the risperidone base is present in the formulation in an amount ranging from 10 wt % to 30 wt %.

14. The formulation of claim 1, wherein the copolymer of lactic acid and glycolic acid has a monomer ratio of lactic acid to glycolic acid ranging from about 100:0 to 60:40, the copolymer has a number average molecular weight ranging from 1000 Daltons to 30,000 Daltons, the organic solvent comprises N-methyl-2-pyrrolidone, and the risperidone base is present in the formulation in an amount ranging from 10 wt % to 30 wt %.

15. The formulation of claim 1, wherein the copolymer of lactic acid and glycolic acid has a monomer ratio of lactic acid to glycolic acid ranging from 100:0 to 75:25, the copolymer has a number average molecular weight ranging from 5000 Daltons to 30,000 Daltons, the organic solvent comprises N-methyl-2-pyrrolidone, and the risperidone base is present in the formulation in an amount ranging from 10 wt % to 30 wt %.

16. The formulation of claim 1, wherein the copolymer of lactic acid and glycolic acid has a monomer ratio of lactic acid to glycolic acid ranging from 100:0 to 75:25, the organic solvent comprises N-methyl-2-pyrrolidone, and the risperidone base is present in the formulation in an amount ranging from 10 wt % to 30 wt %.

17. The formulation of claim 1, wherein the formulation exhibits a lag time less than 0.2.

* * * * *